United States Patent
Rothermel et al.

(10) Patent No.: US 9,446,214 B2
(45) Date of Patent: Sep. 20, 2016

(54) PATIENT INTERFACE DEVICE INCLUDING A MOVEABLE WEDGE FOREHEAD ADJUSTMENT ASSEMBLY

(75) Inventors: Justin Edward Rothermel, Monroeville, PA (US); Chad Zediker, Greensburg, PA (US); Steven Charles Stegman, Gibsonia, PA (US); Christopher James Kadamus, Jamaica Plain, MA (US); Gabor Zanoni, Cambridge, MA (US); Mark Bui Breneman, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 323 days.

(21) Appl. No.: 14/005,373

(22) PCT Filed: Feb. 28, 2012

(86) PCT No.: PCT/IB2012/050919
§ 371 (c)(1),
(2), (4) Date: Sep. 16, 2013

(87) PCT Pub. No.: WO2012/127338
PCT Pub. Date: Sep. 27, 2012

(65) Prior Publication Data
US 2014/0000617 A1    Jan. 2, 2014

Related U.S. Application Data

(60) Provisional application No. 61/453,982, filed on Mar. 18, 2011.

(51) Int. Cl.
*A62B 18/02* (2006.01)
*A61M 16/06* (2006.01)
*A61M 16/00* (2006.01)

(52) U.S. Cl.
CPC ..... *A61M 16/0683* (2013.01); *A61M 16/0057* (2013.01); *A61M 16/06* (2013.01); *A61M 16/065* (2014.02); *A61M 16/0616* (2014.02)

(58) Field of Classification Search
CPC ......... A61M 16/183; A61M 16/0683; A61M 16/0627; A61M 16/06; A61M 16/0655; A61M 16/0057; A61M 16/00
USPC ....... 128/207.11, 206.21, 206.23–28, 205.25
See application file for complete search history.

(56) References Cited

U.S. PATENT DOCUMENTS

2007/0044804 A1* 3/2007 Matula .............. A61M 16/0638
                                                    128/206.21
2008/0135050 A1* 6/2008 Hitchcock ............ A61M 16/06
                                                    128/207.11
2008/0314390 A1 12/2008 Kwok

* cited by examiner

*Primary Examiner* — Jason Flick
*Assistant Examiner* — Victoria Leszczak
(74) *Attorney, Agent, or Firm* — Michael W. Haas

(57) ABSTRACT

A patient interface device is provided that includes a patient sealing assembly, such as a mask having a rigid shell and a cushion coupled to the rigid shell, and a forehead support movably coupled to the patient sealing assembly. The forehead support is moved by an wedge-type adjustment mechanism such that linear translation of the wedge moves the forehead support among the plurality of positions and fixes the forehead support in a desired position among the plurality of positions.

8 Claims, 6 Drawing Sheets

PATIENT INTERFACE DEVICE INCLUDING A MOVEABLE WEDGE FOREHEAD ADJUSTMENT ASSEMBLY

CROSS-REFERENCE TO RELATED APPLICATIONS

This patent application claims the priority benefit under 35 U.S.C. §371 of international patent application. No. PCT/IB2012/050919, filed. Feb. 28. 2012, which claims the priority benefit under 35 U.S.C. §119(e) of U.S. Provisional Application No. 61/453,982 filed on Mar. 18, 2011, the contents of which are herein incorporated by reference.

BACKGROUND OF THE INVENTION

1. Field of the Invention

The present invention relates to patient interface devices for communicating a flow a gas with an airway of a user, and, in particular, to a patient interface device including a moveable wedge forehead adjustment mechanism for adjusting a position of a forehead support relative to a shell or sealing element of the patient interface device.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Because such patient interface devices are typically worn for an extended period of time, it is important for the headgear to maintain the mask component of the device in a tight enough seal against the patient's face without discomfort. One area where fit and comfort is often a concern is the bridge of the patient's nose, as most patient interface devices will apply a pressure to this area. If this pressure is not able to be managed effectively, either or both of a poor fit or patient discomfort will result, thereby limiting the effectiveness of the device in providing a desired treatment as well as discouraging a patient from using the device as prescribed.

SUMMARY OF THE INVENTION

Accordingly, it is an object of one or more embodiments of the present invention to provide a patient interface device that includes a patient sealing assembly, such as, without limitation, a mask having a rigid shell, and a sealing element, such as a cushion, coupled to the rigid shell. A forehead support is movably coupled to the patient sealing assembly. The forehead support is movable among a plurality of positions with respect to the patient sealing assembly. An adjustment mechanism is provided that is adapted to move the forehead support among the plurality of positions and fix the forehead support in a desired position among the plurality of positions.

In an exemplary embodiment, the forehead support is coupled to the shell at or about a top portion of the cushion. The forehead support includes an elongate arm member having a first end movably coupled to the rigid shell and an opposite second end. A forehead pad is coupled at or about the opposite second end of the arm member. The forehead pad has a surface adapted to contact a forehead of the patient. The present invention contemplates that the patient sealing assembly is a nasal mask, a nasal/oral mask, a nasal cushion or a full face mask.

In an exemplary embodiment, the adjustment mechanism includes a wedge member disposed between the forehead support and a portion of the rigid shell such that the wedge member is movable among a plurality of positions with respect to the rigid shell. When disposed in each position of the plurality of positions, the wedge member fixes the forehead support in a respective one of the plurality of positions. The adjustment mechanism further includes a threaded member rotatable about a central axis. The wedge member comprises a threaded aperture cooperatively engaged with the threaded member such that rotation of the threaded member about the central axis causes the wedge member to translate along the central axis.

The threaded member may include an adjustment knob coupled thereto. The wedge member may comprise a first side slidably engaged to a portion of the rigid shell and another side, different from the first side, slidably engaged to a portion of the forehead support. The forehead support may include an elongate arm member and the wedge member may cooperatively engage the arm member in manner such that translation of the wedge member along the central axis in a direction generally toward the patient sealing assembly causes the forehead support to move generally away from the central axis and translation of the wedge member along the central axis in a direction generally away from the patient sealing assembly causes the forehead support to move generally toward the central axis.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
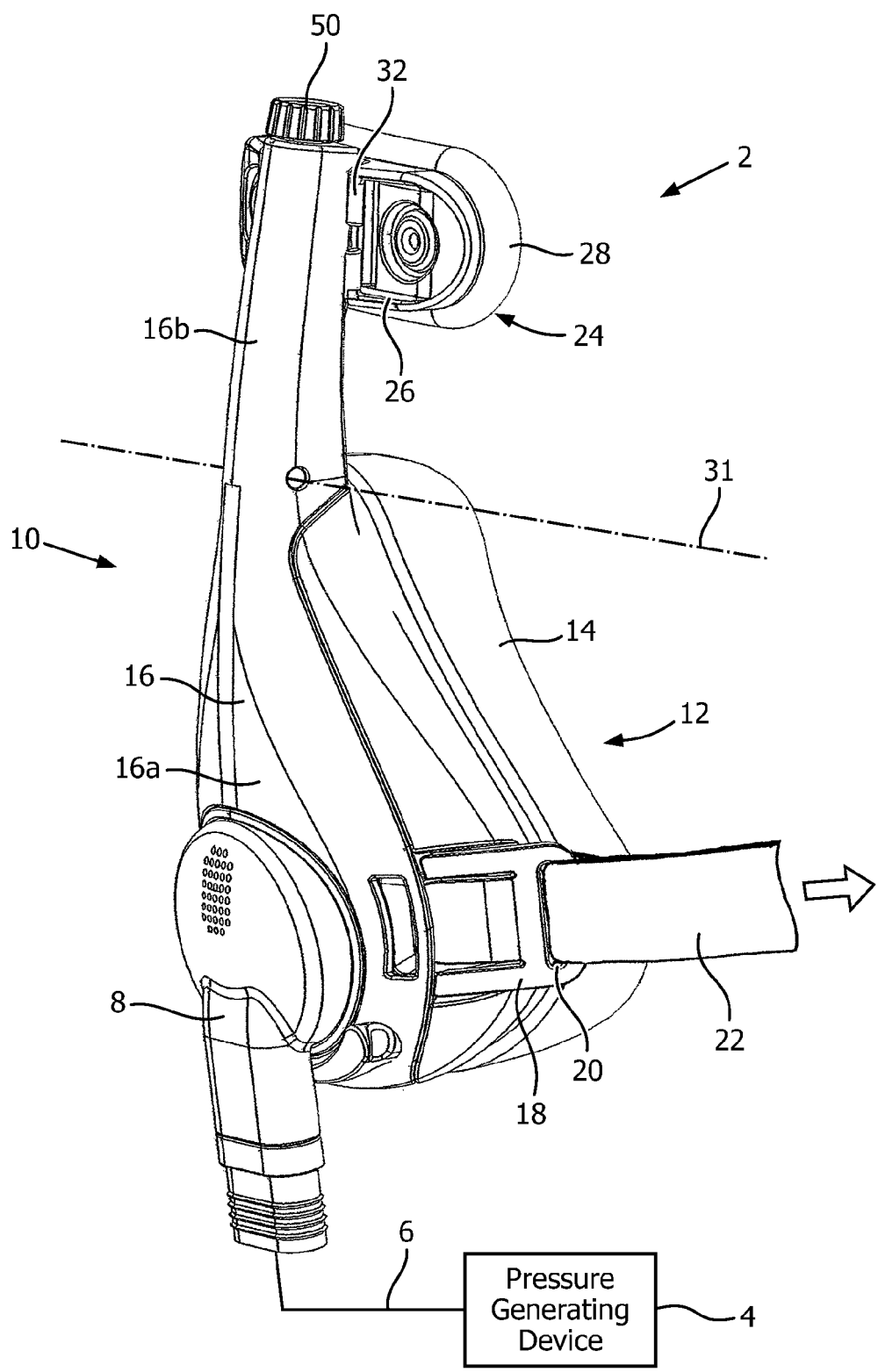
FIGS. 1-3 are isometric, front, and side schematic diagrams, respectively, of a system adapted to provide a regimen of respiratory therapy to a patient according to one embodiment of the invention.

Directional phrases used herein, such as, for example and without limitation, top, As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As employed herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality). Directional phrases used herein, such as, for example and without limitation, top, bottom, left, right, upper, lower, front, back, and derivatives thereof, relate to the orientation of the elements shown in the drawings and are not limiting upon the claims unless expressly recited therein. Like numbers refer to like elements throughout.

Figure 2:
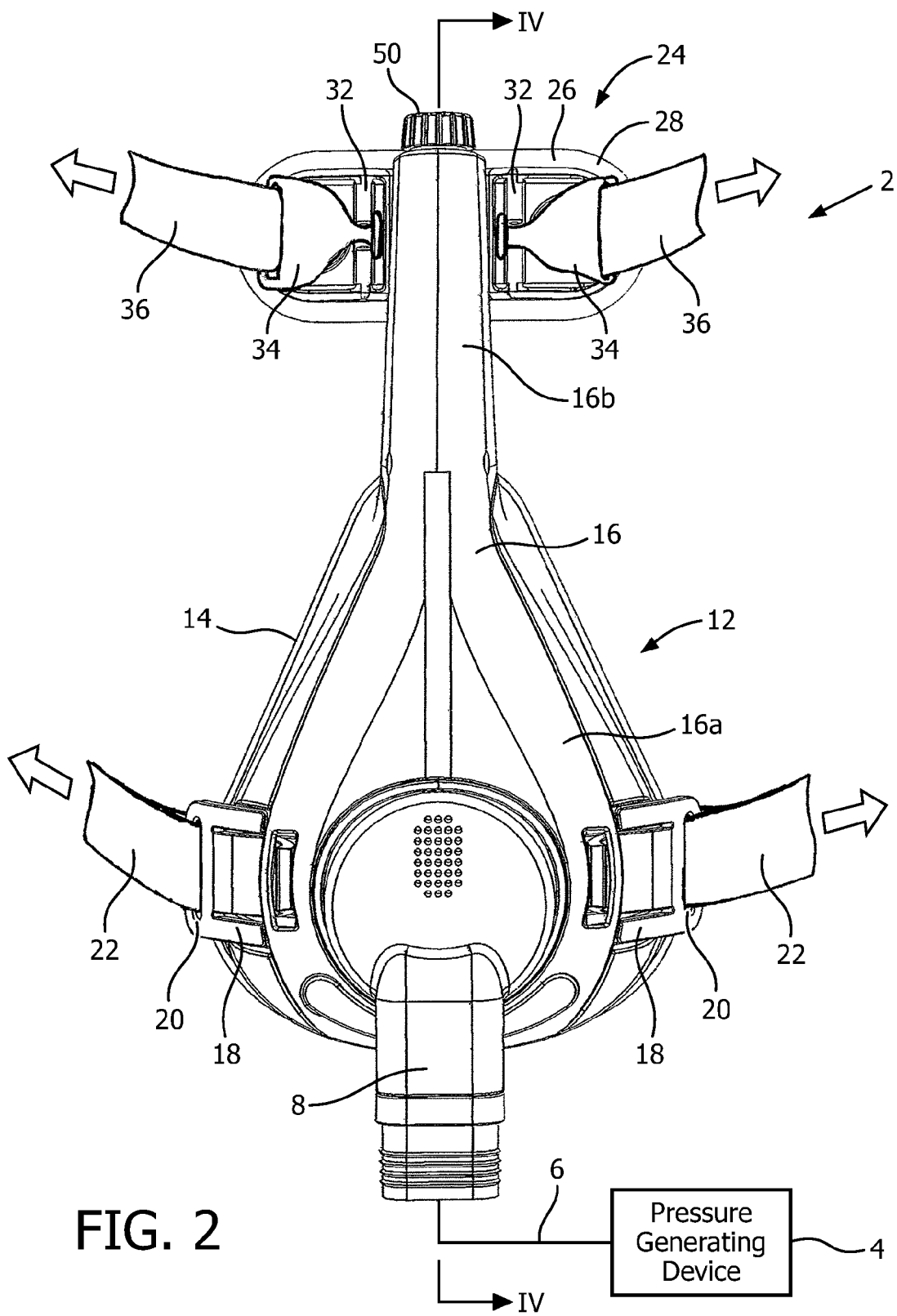
Figure 3:
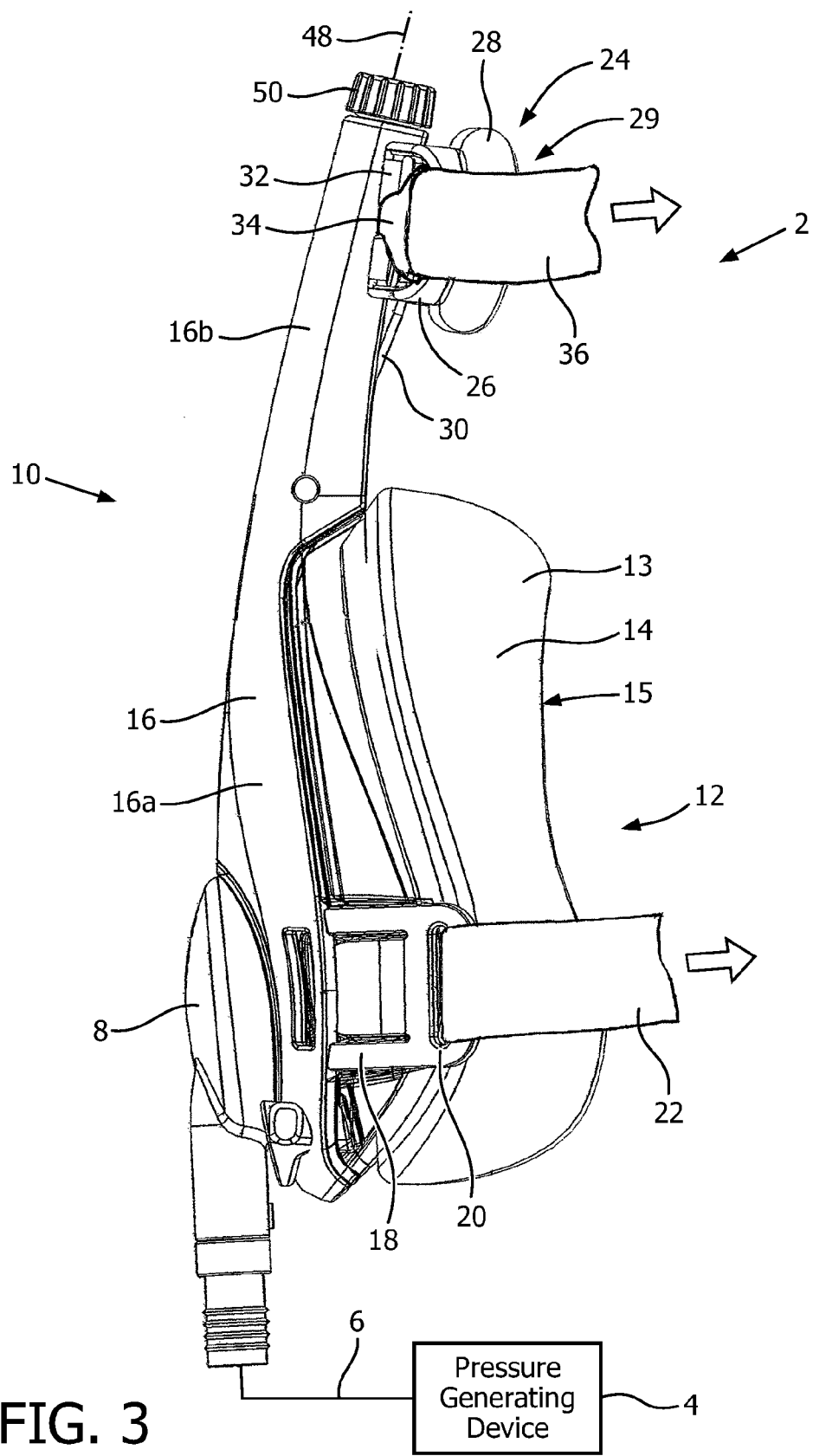

An exemplary embodiment of a system 2 adapted to provide a regimen of respiratory therapy to a patient according to the principles of the present invention is generally shown in FIGS. 1-3. System 2 includes a pressure generating device 4, a delivery conduit 6 coupled to an elbow connector 8, and a patient interface device 10. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 10 through elbow connector 8 and may include, without limitation, flexible tubing. Elbow connector 8 is preferably coupled to patient interface device 10. Delivery conduit 6, elbow connector 8 and patient interface device 10 are often collectively referred to as a patient circuit (not numbered).

Patient interface device 10 includes a patient sealing assembly, which in the illustrated, embodiment is a mask 12 in the form of a nasal/oral mask that seals over the nose and mouth. However, any type of patient sealing assembly, such as a nasal mask that seals over the nose only, which facilitates the delivery of the flow of breathing gas to the airway of a patient, may be substituted for mask 12 while remaining within the scope of the present invention. Mask 12 includes a sealing means for creating a seal against the skin. In the illustrated embodiment, the sealing means is a cushion 14 coupled to a rigid shell 16. The present invention contemplates that other technique for creating a seal against the user are contemplated by the present invention, such as nasal pillows or cannula that seal over the nares, multi-flap cushions, and cushions having any number of configurations and materials are contemplated by the present invention.

An opening (not numbered) in shell 16 is provided to which elbow connector 8 is coupled. The opening allows the flow of breathing gas from pressure generating device 4 to be communicated to an interior space (not numbered) defined by shell 16 and cushion 14, and then to the airway of a patient on which patient interface device 10 is disposed. In addition, cushion 14 includes a sealing surface 15 (FIGS. 3 and 4) that is structured to engage the face of a patient when patient interface device 10 is donned by the patient.

Shell 16 generally includes a lower portion 16a, to which cushion 14 is coupled, and coupling portion 16b which extends upward from lower portion 16a generally a distance above cushion 14. Lower portion 16a includes first and second headgear mounting tabs 18, each having a slot 20 structured to receive and hold a respective lower headgear strap 22 of a headgear component used to secure patient interface device 10 to the head of the patient. It is to be understood that the present invention contemplated any technique or configuration for coupling the headgear to shell 16.

While coupling portion 16b is shown disposed as the portion of the shell that is generally proximate to the bridge of the nose when the patient interface device is donned by the user, the present invention contemplates that the coupling portion can be provided at other locations. The present invention also contemplates that the coupling portion is intergral with the remainder of the shell or is a separate element that is affixed to the mask shell, either permanently or removeably. Moreover, other configurations, geometries, structures and sizes are contemplated for coupling portion 16b. For example, coupling portion 16b can include a pair of arms protruding from or attached to the mask shell.

Patient interface device 10 further includes a forehead support 24 that, in the illustrated embodiment, includes support frame 26 having a forehead cushion 28 coupled thereto. Forehead support 24 is structured to provide additional support for patient interface device 10 by engaging the forehead of the patient via a forehead contacting surface 29 of forehead cushion 28. Support frame 26 is coupled to an arm member 30, which in turn is movably (in the illustrated embodiment pivotably) coupled to shell 16. More particularly, preferably a first end 30a of arm member 30 is movably coupled to shell 16 at or about the same elevation as the top (apex) portion 13 of cushion 14, and support frame 26 is coupled to an opposite second end 30b of arm member 30. In the illustrated embodiment, arm member 30 moves in a pivotal manner about a pivot axis 31 (FIGS. 1 and 5).

In the illustrated exemplary embodiment, support frame 26 includes fastening mechanisms 32 provided at opposite ends thereof Each fastening mechanism 32 is structured to receive a respective clip member 34 having an upper headgear strap 36 of the headgear component coupled thereto, such as shown in FIG. 2. As is known, lower headgear straps 22 and upper headgear straps 36 enable the headgear component of which they are a part to secure patient interface device 10 to the patient's head. It is to be understood that the present invention contemplates any technique or configuration for coupling the headgear the support frame. The present invention also contemplates that the fastening mechanisms can be omitted entirely. In order to selectively adjust and fix the position of forehead support 24 with respect to the patient sealing assembly, and thus conversely adjust the relative positioning of the patient sealing assembly with respect to forehead support 24, patient interface device 10 includes an adjusting means in the form of an adjustment mechanism 40, as shown in the magnified view of FIG. 5 in which coupling portion 16b has been generally removed to show detail.

Figure 4:
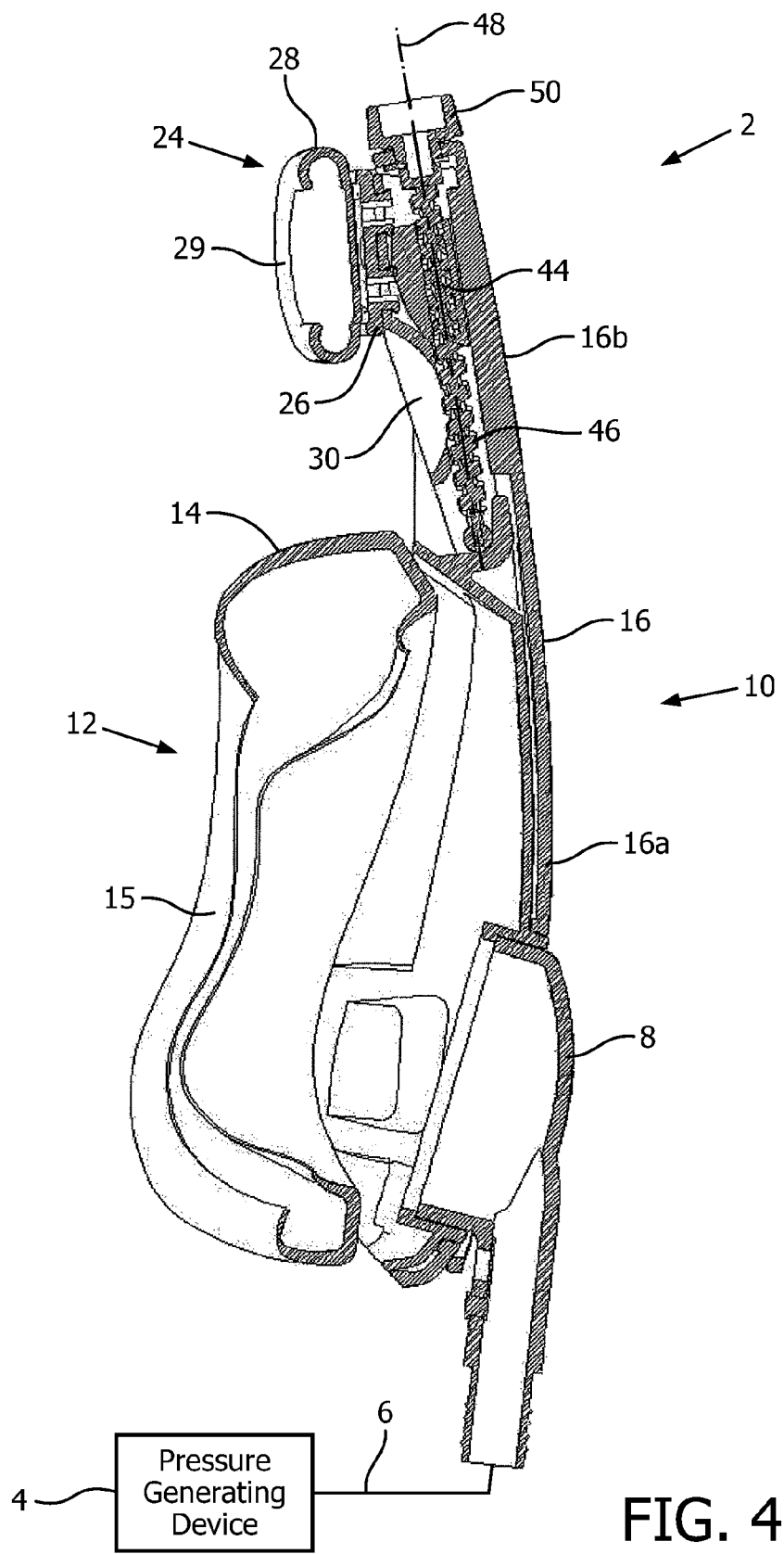
FIG. 4 is a sectional schematic diagram of the system taken along line 4-4 of FIG. 2.
Figure 5:
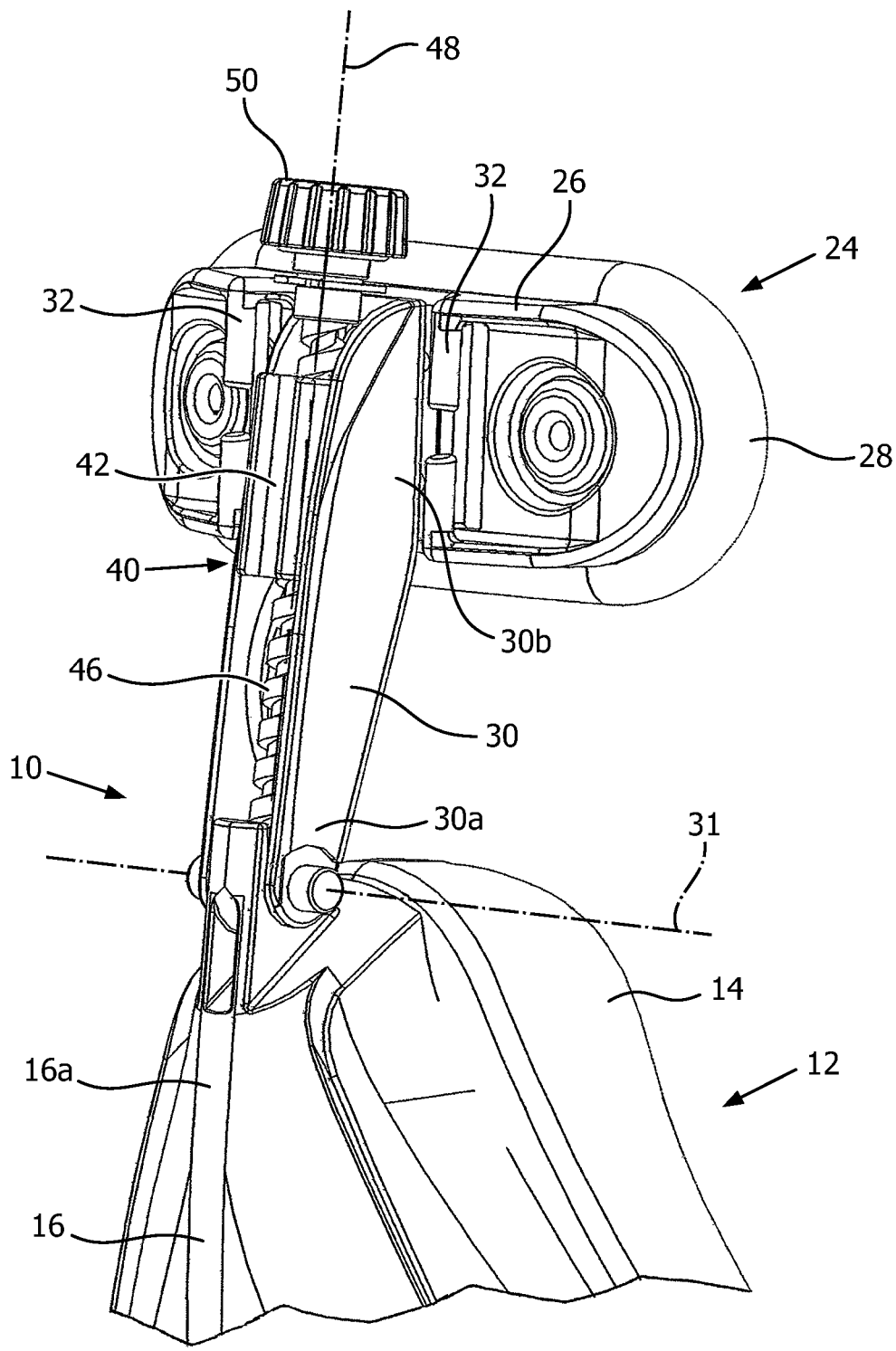
FIG. 5 is magnified view of a forehead support portion forming a part of the exemplary patient interface device embodiment employed in the system embodiment of FIGS. 1-3 with an upper portion of a shell removed to show detail of the forehead support portion.

Referring to FIGS. 4 and 5, adjustment mechanism 40 includes a wedge member 42 having a threaded aperture 44, and an elongate threaded member 46 that function as a wedge moving means to cause the wedge to move relative to coupling portion 19b. Elongate threaded member 46 is disposed in a generally vertical position adjacent arm member 30 and is rotatable about a central rotational axis 48. Wedge member 42 is disposed such that threaded aperture 44 thereof cooperatively engages threaded member 46. Accordingly, wedge member 42 is disposed generally between arm member 30 and coupling portion 16b, preferably such that a first side (not numbered) of wedge member 42 slidingly engages coupling portion 16b and at least one other side (not numbered) of wedge member 42 cooperatively engages arm member 30 in a sliding manner. The threaded engagement between wedge member 42 and threaded member 46 provides for wedge member 42 to be movable among a number of positions along central rotational axis 48 as a result of rotation of threaded member 46 about central rotational axis 48. To assist such rotation of threaded member 46, an adjustment knob 50 is preferably provided at the upper end (not numbered) of threaded member 46.

Figure 6A:
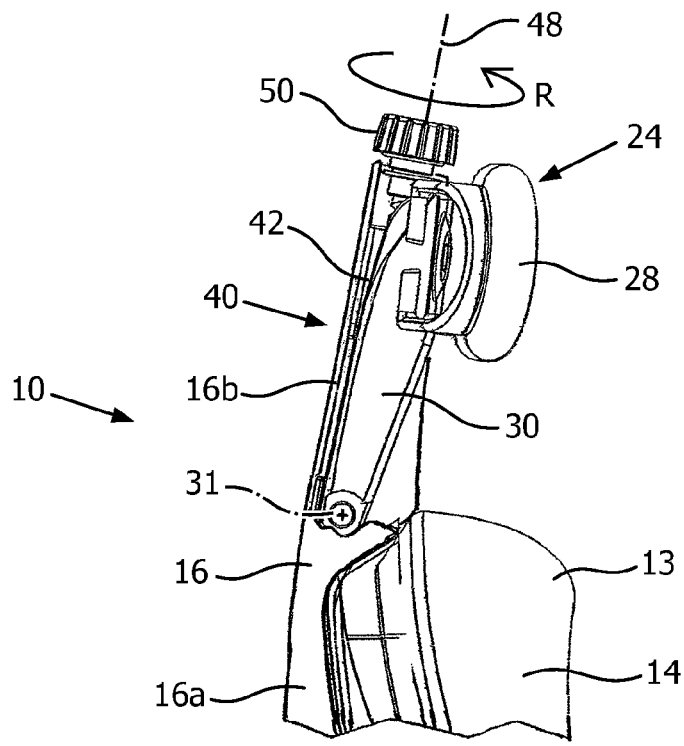
FIGS. 6a and 6b are side views of a portion of the exemplary patient interface device embodiment employed in the system embodiment of FIGS. 1-3 showing an exemplary forehead support disposed in different positions.
Figure 6B:
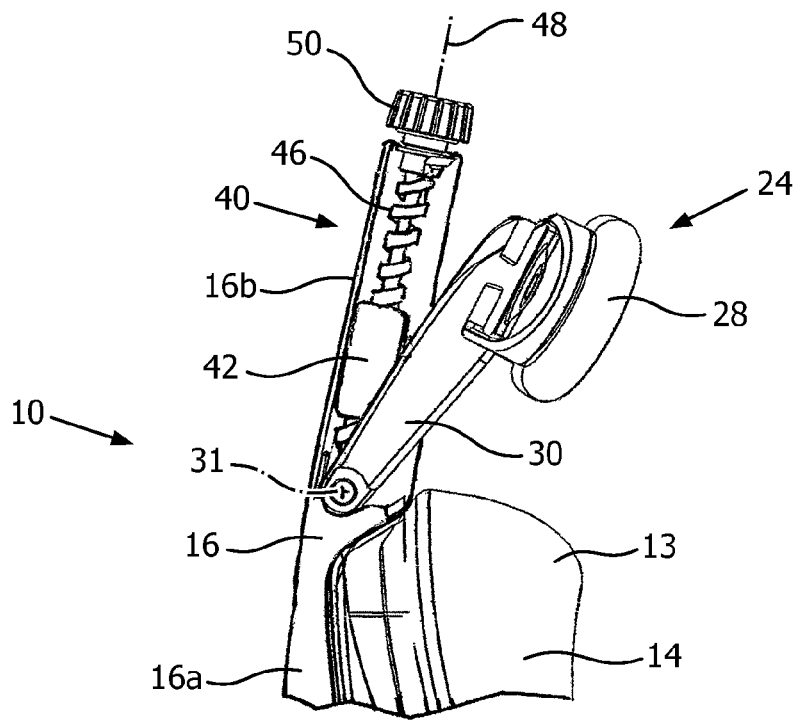

FIGS. 6a and 6b show the basic operation of adjustment mechanism 40 to selectively adjust and fix the position of forehead support 24 with respect to the patient sealing assembly. For example, FIG. 6a shows forehead support positioned in a first example position generally near central rotational axis 48. In such position, wedge member 42 is positioned generally near the top (not numbered) of threaded member 44 near adjustment knob 50. By rotating adjustment knob 50 (such as could be readily done by a patient wearing patient interface device 10) about central rotational axis 48 in a counterclockwise direction (when viewed from above), as shown by arrow R in FIG. 6a, wedge member 42 is moved along central rotational axis 48, generally toward the patient sealing assembly. As a result of the cooperative engagement between wedge member 42 and arm member 30, arm member 30 is moved generally away from central rotational axis 48 as wedge member 42 moves toward the patient sealing assembly, as shown in FIG. 6b where forehead support 24 has now been positioned in a second example position, generally away from central rotational axis 48. Conversely, if a patient desired to position forehead support 24 closer to central rotational axis 48, the patient would simply rotate adjustment knob 50 in a clockwise direction, thus causing wedge member 42 to move away from the patient sealing assembly and thus, due to the cooperative engagement previously discussed, pull arm member 30 toward central rotational axis 48.

The adjustment mechanism 40 and cooperating parts of patient interface device 10 as just described provides a mechanism for selectively (and finely) adjusting the force applied to the bridge of the nose of a patient by upper (apex) portion 13 of cushion 14 of mask 12 by varying the relative positioning of forehead support 24 with respect to mask 12. The ability to provide subtle adjustments helps to minimize leaks and provide comfort to the patient. More specifically, patient interface device 10 is coupled to the head of a patient generally at a lower portion adjacent a lower part (not numbered) of cushion 14 via lower strap members 22 and at an upper portion, at forehead cushion 28, which is secured to the forehead of a patient via upper strap members 36. As forehead cushion 28 is generally a fixed point of contact with the patient (due to upper strap members 36), adjustment of forehead support 24 toward a position near central rotational axis 48, such as shown in FIG. 6a for example, generally forces upper (apex) portion 13 of cushion 14 toward the bridge of the patient's nose (thus increasing pressure on the bridge of the nose). Conversely, adjustment of forehead support 24 to a position generally away from central rotational axis 48, such as shown in FIG. 6b for example, generally forces upper (apex) portion 13 of cushion 14 away from the bridge of a patient's nose (thus reducing pressure on the bridge of the nose).

While an embodiment having an exemplary adjustment mechanism has been described in detail herein, it should be understood that other embodiments are also possible within the scope of the present invention. Thus, as used herein, the term "adjustment mechanism" shall mean any mechanism that adjusts the position of the forehead cushion with respect to the patient sealing assembly.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:
1. A patient interface device, comprising:
   a patient sealing assembly adapted to communicate a flow of breathing gas with an airway of a patient;
   a coupling portion fixed to the patient sealing assembly;
   a forehead support pivotably coupled to the patient sealing assembly, the forehead support pivotable among a plurality of positions with respect to the patient sealing assembly; and
   an adjustment mechanism adapted to move the forehead support among the plurality of positions and fix the forehead support in a desired position among the plurality of positions, wherein the adjustment mechanism comprises:
   a wedge member movable among a plurality of positions with respect to the patient sealing assembly, the wedge member having a first side slidably engaged with the coupling portion and another side, different from the first side, slidably engaged to a portion of the forehead support, wherein the wedge member is disposed between the forehead support and the coupling portion, and wherein the wedge member engages the forehead support causing the forehead support to move among the plurality of positions; and
   a threaded member rotatable about a central axis, wherein the wedge member comprises a threaded aperture cooperatively engaged with the threaded member, and wherein rotation of the threaded member about the central axis causes the wedge member to translate along the central axis.

2. The patient interface device according to claim 1, wherein the patient sealing assembly comprises a mask having a rigid shell and a sealing element coupled to the rigid shell.

3. The patient interface device according to claim 2, wherein the forehead support is coupled to the shell at or about a portion of the shell that is structured to be disposed at or about a bridge of a nose of a user responsive to the patient interface device being donned by such a user.

4. The patient interface device according to claim 1, wherein the forehead support comprises:
  an elongate arm member having a first end pivotably coupled to the patient sealing assembly and an opposite second end; and
  a forehead pad coupled at or about the opposite second end of the arm member, the forehead pad having a surface adapted to contact a forehead of the patient.

5. The patient interface device according to claim 1, wherein the threaded member includes an adjustment knob coupled thereto.

6. The patient interface device according to claim 1, wherein the forehead support comprises an elongate arm member, and wherein the wedge member cooperatively engages the arm member in manner such that translation of the wedge member along the central axis in a direction generally toward the patient sealing assembly causes the forehead support to move generally away from the central axis and translation of the wedge member along the central axis in a direction generally away from the patient sealing assembly causes the forehead support to move generally toward the central axis.

7. The patient interface device according to claim 1, wherein the patient sealing assembly comprises a mask having a rigid shell and a sealing element coupled to the rigid shell, and wherein the coupling portion is integral with the rigid shell.

8. The patient interface device according to claim 1, wherein the forehead support is pivotable about a pivot axis and wherein the central axis is oriented perpendicular to the pivot axis.

* * * * *